United States Patent
Ainger et al.

(10) Patent No.: US 11,486,880 B2
(45) Date of Patent: Nov. 1, 2022

(54) METHOD OF MEASURING HARSHNESS OF A SURFACTANT

(71) Applicant: Conopeo, Inc., Englewood Cliffs, NJ (US)

(72) Inventors: Nicholas John Ainger, Wirral (GB); Annie Jaye Galpin, Mancot (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 49 days.

(21) Appl. No.: 17/056,570

(22) PCT Filed: Jun. 26, 2019

(86) PCT No.: PCT/EP2019/067047
§ 371 (c)(1),
(2) Date: Nov. 18, 2020

(87) PCT Pub. No.: WO2020/002453
PCT Pub. Date: Jan. 2, 2020

(65) Prior Publication Data
US 2021/0208155 A1    Jul. 8, 2021

(30) Foreign Application Priority Data

Jun. 28, 2018   (EP) .................................. 18180312

(51) Int. Cl.
*G01N 33/68* (2006.01)
*G01N 21/78* (2006.01)

(52) U.S. Cl.
CPC ......... *G01N 33/6839* (2013.01); *G01N 21/78* (2013.01); *G01N 2333/415* (2013.01)

(58) Field of Classification Search
CPC ....... G01N 2333/415; G01N 2333/425; G01N 33/68; G01N 33/6839; G01N 21/77; G01N 21/78
USPC .......................................... 436/86, 164, 166
See application file for complete search history.

(56) References Cited

U.S. PATENT DOCUMENTS 8,778,277 B2 *   7/2014   Jones ................. G01N 33/6833
                                                            436/175
2007/0212304 A1 *  9/2007   Goldberg ............ A61K 49/0006
                                                            436/164

FOREIGN PATENT DOCUMENTS

WO    WO2011146461    11/2011

OTHER PUBLICATIONS

Moore et al. Langmuir, vol. 19, pp. 1009-1016, 2003.*
Search Report and Written Opinion in EP18180312; dated Sep. 7, 2018.
Xu Helan et al.; Biodegradable hollow zein nanoparticles for removal of reactive dyes from wastewater; Journal of Environmental Management; Apr. 30, 2013; 33-40; 125.
Zein in controlled drug delivery and tissue engineering; Journal of Controlled Release; Jun. 30, 2014; 108-122; 189.
Zein-based solid dispersion for potential applicationin targeted delivery; Journal of Pharmaceutical Investigation; Feb. 27, 2017; 357-364; 47, No. 4.
Corn Proteins; Industrial and Engineering Chemistry; Jun. 1, 1937; 673-674; 29, No. 6.
S.K. Mehta, Bhawna; Significant effect of polar head group of surfactants on the solubilization of Zein in mixed micellar (SDS-DDAB) media; Colloids and Surfaces B: biointerfaces; Nov. 1, 2010; 74-80; 81, No. 1; Elsevier.
Search Report and Written Opinion PCTEP2019067047; dated Aug. 13, 2019.
Xu Helan et al; Biodegradable hollow zein nanoparticles for removal of reactive dyes from wastewater; Biodegradable hollow zein nanoparticles for removal of reactive dyes from wastewater; Apr. 30, 2013; pp. 33-40; 125.
Metha S K et al; Significant effect of polar head group of surfactants on the solubilization of Zein in mixed micellar (SDS-DDAB) media; Significant effect of polar head group of surfactants on the solubilization of Zein in mixed micellar (SDS-DDAB) media; Nov. 1, 2010; pp. 74-80; 81.
J.F. Walsh; Corn Proteins; Corn Proteins; Jun. 1, 1937; pp. 673-674; 29 No. 6.
Paliwal Rishi et al; Zein in controlled drug delivery and tissue engineering; Zein in controlled drug delivery and tissue engineering; Jun. 30, 2014; pp. 108-122; 189.
Nguyen Minh Ngoc-Uyen et al; Zein-based solid dispersion for potential application in targeted delivery; Zein-based solid dispersion for potential application in targeted delivery; Feb. 27, 2017; 357-364; 47 No. 4; Korea (South).

* cited by examiner

*Primary Examiner* — Maureen Wallenhorst
(74) *Attorney, Agent, or Firm* — Foley & Lardner LLP

(57) ABSTRACT

Provided is a quick and accurate way of assessing harshness of a surfactant towards a protein, which can be easily carried out under non-laboratory conditions and which facilitates recommendations for making suitable products. Particularly, provided are methods of measuring the harshness of a surfactant, which includes (a) providing an aqueous solution of surfactant and taking a first colour measurement; (b) adding a solid protein-dye complex to the aqueous solution of surfactant; (c) taking a second colour measurement and measuring the change in colour between the first colour measurement and the second colour measurement; and (d) matching the change in colour with a reference scale. The solid protein-dye complex can be prepared by dissolving a non-denatured corn protein and a protein binding dye in aqueous alcohol, and removing the aqueous alcohol.

11 Claims, No Drawings

METHOD OF MEASURING HARSHNESS OF A SURFACTANT

CROSS-REFERENCE TO RELATED APPLICATIONS

This application is a U.S. National Stage Application under 35 U.S.C. § 371 of International Application No. PCT/EP2019/067047, filed on Jun. 26, 2019, which claims the benefit of European Patent Application No. 18180312.3, filed Jun. 28, 2018, the entire disclosures of which are hereby incorporated by reference for any and all purposes.

FIELD OF INVENTION

The present invention relates to an improved method for determining the harshness of a surfactant. The method has particular application in the field of personal care.

BACKGROUND AND PRIOR ART

Common laboratory tests use a chemical indicator that changes colour when protein is present. The intensity of the colour change indicates the amount of protein present. One commonly used indicator is Bicinchoninic Acid (BCA). Peptide bonds in leached proteins from hair react with copper, reducing $Cu^{2+}$ to $Cu^{1+}$ which reacts with the BCA to produce a purple complex, the intensity of which indicates the amount of protein and therefore, the level of damage to the hair.

WO 11/146461 (Procter &Gamble) discloses a method for demonstrating hair damage by eluting a protein fragment from a hair sample with an aqueous solution and adding a protein indicating reagent to the aqueous solution to provide a visual indicator and comparing the visual indicator to a scale to determine an amount of eluted protein fragments present in the aqueous solution.

Another test, based on so-called "Zein protein", enables the determination of the irritation potential (harshness) of a surfactant or a surfactant-based product (shower gel, shampoo, soap, washing-up liquid, etc.). Zein protein is a yellow corn protein that is similar to the keratin present in the skin and hair. Its physico-chemical characteristics are described in, for example, Metha, S. K. et al: "Significant effect of polar head group of surfactants on the solubilization of Zein in mixed micellar (SDS-DDAB) media"; Colloids and Surfaces B:Biointerfaces 81 (2010) 74-80. The skin irritation potential and protein denaturation potential of the product is directly proportional to the quantity of dissolved proteins. Typically, the protein is first treated with dye and combined with an aqueous solution of the surfactant. The level of harshness of the surfactant is indicated by the amount of dye released such that a darker solution indicates a harsher composition.

Despite the prior art there remains a need for a test that is significantly quicker and that can be easily carried out under non-laboratory conditions, for example, at point of sale of a hair treatment product, or in a salon environment. Such a test could illustrate to the individual consumer straight away the level of irritation of a surfactant containing formulation and enable a suitable product recommendation to be made.

We have now found that by using pre-prepared, solid protein samples containing a protein binding dye to quantify the amount of eluted protein and preferably referring to an irritation reference scale (for example based on the b value), the harshness of the surfactant can be measured more quickly; the method being portable and easily and quickly carried out under a range of non-laboratory environments.

STATEMENT OF INVENTION

In a first aspect, the invention provides a method of measuring the harshness of a surfactant, comprising the steps of:
i) preparing a solid protein-dye complex comprising:
  a) a protein, which is a non-denatured corn protein and which is soluble in aqueous alcohol; and
  b) a protein binding dye, which is specific to the protein (a);
  by dissolving a) and b) in aqueous alcohol to form a solution of protein-dye complex; and removing the aqueous alcohol to form a solid protein-dye complex; and
ii) providing an aqueous solution of surfactant and taking a first colour measurement, iii) adding the solid protein-dye complex to the aqueous solution of surfactant, taking a second colour measurement and measuring the change in colour between the first colour measurement and the second colour measurement; and
iv) matching the change in colour with a reference scale.

The solid protein-dye complex comprising (a) a non-denatured corn protein and (b) a protein binding dye specific to protein (a) is obtainable from a process comprising the steps of dissolving a) and b) in aqueous alcohol to form a solution of protein-dye complex; and removing the aqueous alcohol to form the solid protein-dye complex.

Preferably, the solid protein-dye complex is formed as multiple, i.e. at least 2, preferably from 2 to 100 individual units. The size and shape of the units is such that they are suitable for performing step (iii) of the method of the first aspect of the invention. A preferred size comprises a maximum dimension of from 5 to 100 mm, more preferably 10 to 50 mm. The units may be any desired shape, preferably selected from disc shaped, spherocylinder shaped, letter shaped, number shaped and logo shaped.

In one embodiment, multiple units are provided in a uniform size and shape. The solid protein-dye complex may be packaged, preferably in a pack containing 2 or more units, preferably from 2 to 100 of solid protein-dye complex.

It is an advantage of the composition and method of the invention that the solid protein-dye complex is stable over time, preferably for at least 6 months, more preferably for at least one year at ambient temperature. Thus it can be premade and, for example, transported to the site of a demonstration or measurement, where the method starting from step (iii) can be carried out.

General Description of the Invention
The Method
The method of the invention measures the harshness of a surfactant.

The method of the invention comprises the additional step of matching the colour with a reference scale to determine a harshness of the surfactant, based on the intensity of the colour in the solution. The reference scale may include a series of alphanumeric symbols, each indicating a different level of harshness. Alternatively, a series of colour patches of increasing intensity wherein each patch corresponds to an ascending level of harshness.

The reference scale may be a digital scale. The matching of the colour to the reference scale may be done by electronic means, for example by using an imaging device or smart phone camera.

Other suitable means of matching to the reference scale include a visual assessment, photographic means, absorbance or transmittance measurement (for example using an electronic device), a spectrophotometer or fluorimeter and measurement of the b parameter in CIE-LAB colour space, preferably measurement of the b parameter in CIE-LAB colour space.

The method of the invention preferably comprises the additional step of making a product recommendation based on the level of harshness determined under step (iii).

A preferred method of the invention is a method of measuring internal hair damage, comprising the steps of:
 i) preparing a solid protein-dye complex comprising:
  a) a protein, which is a non-denatured corn protein and which is soluble in aqueous alcohol; and
  b) a protein binding dye, which is specific to the protein (a);
 by dissolving a) and b) in aqueous alcohol to form a solution of protein-dye complex; and
 removing the aqueous alcohol to form a solid protein-dye complex; and
 ii) providing an aqueous solution of surfactant and taking a first colour measurement;
 iii) adding the solid protein-dye complex to the aqueous solution of surfactant, taking a second colour measurement and measuring the change in colour between the first colour measurement and the second colour measurement;
 iv) matching the change in colour with a reference scale to determine a level of harshness of the surfactant, based on an amount of eluted dye in the water; and
 v) making a product recommendation based on the level of harshness determined under step (iii).

Preferably the surfactant is a in a composition comprising the surfactant. In a preferred embodiment the composition comprising the surfactant is intended to be applied to hair as part of a regular hair wash and care or treatment regime. Preferably the composition is a hair shampoo, for use on human head hair.

Any concentration of surfactant can be used but preferably the raw material surfactant or the composition comprising the surfactant is diluted between 5 and 20 times. This advantageously mimics in-use conditions. A higher concentration of surfactant may be used for purposes where a faster reaction is required, for example demonstration purposes.

In one embodiment the method comprises a step of capturing one or more images of one or more steps of the method of the invention and storing and/or transmitting the one or more images. The image(s) may, for example, be stored on a recordable medium such as CD, flash drive or other computer-readable memory or on social media. The image(s) may be transmitted, for example, for display on one or more visible display units. Suitable visible display units include, for example, monitors, TV screens and/or mobile device screens. Preferably, the image(s) are used in advertising.

The Protein

The protein is a non-denatured, corn protein, that is soluble in aqueous alcohol, preferably Zein protein. Zein protein is readily available, for example from Merck.

The protein is soluble in aqueous alcohol, preferable ethanol, preferably bioethanol.

The Protein Binding Dye

The protein binding dye is specific to the protein.

Suitable dyes include triarylmethane dyes. Preferred triarylmethane dyes are selected from methyl violet dyes and malachite green dyes. Preferred methyl violet dyes are selected from Methyl Violet 2B, Methyl Violet 6B and Methyl Violet 10B. Preferred malachite green dyes are selected from Malachite Green, Brilliant Green, Brilliant Blue, Coomassie Blue R and Coomassie Blue G, preferably Coomassie Blue R. The most preferred dye for use with Zein protein is Coomassie Blue R dye.

The protein and the protein binding dye are dissolved in aqueous alcohol to form a protein/dye solution. The alcohol preferably has from 1 to 6 carbon atoms and is most preferably ethanol.

The alcohol is then removed, preferably by evaporation to form a solid protein-dye complex, preferably by air drying, for example in an oven. Suitable means do not denature the protein.

Preferably, the protein/dye solution is first applied to a substrate, for example a mould before being dried. One type of mould is a petri dish. The resultant solid protein-dye complex can then be removed before use in step (iii) of the method of the invention.

The solid protein-dye complex is then added to an aqueous solution of surfactant and left, preferably without agitation, for a period of time. Preferably the period of time is from 1 to 30 min, more preferably for 1 to 10 min.

The Surfactant

The method of the invention can be used to determine the harshness of a single surfactant or a mixture of surfactants.

The surfactant is preferably incorporated into a composition. The method may use any surfactant containing composition, preferably a personal care composition, preferably selected from a body wash, a hair cleaning composition, a handwash and a soap or a home care composition, preferably selected from a laundry cleaning composition, a washing-up liquid and a hard surfaces cleaner. Most preferably the composition is a hair cleaning composition, most preferably a shampoo.

Surfactants are compounds which have hydrophilic and hydrophobic portions that act to reduce the surface tension of the aqueous solutions they are dissolved in. Typically, surfactant compositions for use in the method of the invention will generally comprise one or more cleansing surfactants, which are cosmetically acceptable and suitable for topical application to the hair. The cleansing surfactant may be chosen from anionic, non-ionic, amphoteric and zwitterionic compounds and mixtures thereof.

Non-limiting examples cleansing surfactants, typically used hair cleansing and skin cleansing compositions include anionic cleansing surfactants including; alkyl sulphates, alkyl ether sulphates, alkaryl sulphonates, N-alkyl sarcosinates, alkyl phosphates, alkyl ether phosphates, acyl amino acid based surfactants, alkyl ether carboxylic acids, acyl taurates, acyl glutamates, alkyl glycinates and salts thereof, especially their sodium, magnesium, ammonium and mono-, di- and triethanolamine salts. The alkyl and acyl groups in the preceding list generally contain from 8 to 18, preferably from 10 to 16 carbon atoms and may be unsaturated. The alkyl ether sulphates, alkyl ether phosphates and alkyl ether carboxylic acids and salts thereof may contain from 1 to 20 ethylene oxide or propylene oxide units per molecule.

Further non-limiting examples of cleansing surfactants may include non-ionic cleansing surfactants including; aliphatic ($C_8$-$C_{18}$) primary or secondary linear or branched chain alcohols with alkylene oxides, usually ethylene oxide and generally having from 6 to 30 ethylene oxide groups. Other representative cleansing surfactants include mono- or di-alkyl alkanolamides (examples include coco mono-ethanolamide and coco mono-isopropanolamide) and alkyl polyglycosides (APGs). Suitable alkyl polyglycosides for use in the invention are commercially available and include for example those materials identified as: Plantapon 1200 and Plantapon 2000 ex BASF. Other sugar-derived surfactants, which can be used in the method of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

Additional non-limiting examples of cleansing surfactants include amphoteric or zwitterionic cleansing surfactants including; alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms.

Typical cleansing surfactants for use in compositions for use in the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium cocoyl isethionate, sodium lauryl isethionate, lauryl ether carboxylic acid and sodium N-lauryl sarcosinate, sodium pareth sulphate, cocodimethyl sulphopropyl betaine, lauryl betaine, coco betaine, cocamidopropyl betaine, sodium cocoamphoacetate.

Preferred cleansing surfactants are sodium lauryl sulphate, sodium lauryl ether sulphate, sodium lauryl ether sulphosuccinate, ammonium lauryl sulphate, ammonium lauryl ether sulphate, sodium cocoyl isethionate and lauryl ether carboxylic acid, coco betaine, cocamidopropyl betaine, sodium cocoamphoacetate.

Mixtures of any of the foregoing anionic, non-ionic and amphoteric cleansing surfactants may also be suitable.

EXAMPLES

Embodiments of the invention will now be illustrated with reference to the following non-limiting example.

All materials were obtained from BASF or Sigma-Aldrich (Merck).

Zein powder (10 wt %) and Coomassie Blue R dye (0.1%) were added to a glass jar, and made up to 100 wt % with 90:10 aqueous ethanol (90 ethanol: 10 water). The mixture was left to disperse with stirring for 12 hours to produce protein-dye complex solution.

2 g of the protein-dye complex solution was added to four petri dishes and dried overnight under ambient conditions. The dried discs of protein-dye complex were then removed from the petri dishes and stored until required.

Dilutions (10 wt %) of four surfactants were prepared and a first colour measurement of each dilution was taken using CIEL*a*b on a Konica Minolta spectrometer.

A disc of protein-dye complex was added to each surfactant dilution, and soaked for 15 minutes. A second colour measurement was obtained of the resulting solutions. The decrease in b* value between the first and second colour measurement indicated the increase in blue colour. The lower the b value the 'bluer' the sample and the harsher the formulation. Three samples from each surfactant solution were measured as replicates.

| Data Name | Average Δb* | St Deviation |
|---|---|---|
| SLES (1EO) | −43.64 | 1.21249055 |
| SLES (3EO) | −33.175 | 1.045035885 |
| SDS | −49.465 | 0.883529852 |
| Decyl Glucoside | −11.2625 | 0.84072885 |

It will be seen that differences in the harshness of the surfactants are easily and quickly apparent.

The invention claimed is:

1. A method of measuring harshness of a surfactant, comprising the steps of:
   i) preparing a solid protein-dye complex comprising:
      a) a protein, which is a non-denatured corn protein and which is soluble in aqueous alcohol; and
      b) a protein binding dye, which binds specifically to the protein (a);
   by dissolving a) and b) in aqueous alcohol to form a solution of protein-dye complex; and
   removing the aqueous alcohol to form a solid protein-dye complex;
   ii) providing an aqueous solution of a surfactant and taking a first colour measurement of the aqueous solution;
   iii) adding the solid protein-dye complex to the aqueous solution of the surfactant, taking a second colour measurement of the aqueous solution and measuring a change in intensity of the colour between the first colour measurement and the second colour measurement; and
   iv) matching the change in intensity of the colour with a reference scale to determine the harshness of the surfactant.

2. The method as claimed in claim 1, wherein the protein binding dye is selected from the group consisting of Methyl Violet 2B, Methyl Violet 6B, Methyl Violet 10B, Malachite Green, Brilliant Green, Brilliant Blue, Coomassie Blue R and Coomassie Blue G.

3. The method as claimed in claim 2, wherein the protein binding dye is Coomassie Blue R.

4. The method as claimed in claim 1, wherein matching the change in intensity of the colour with a reference scale comprises matching the change in intensity of the color in the aqueous solution of the surfactant, with a color intensity on the reference scale, wherein a darker solution indicates a harsher surfactant.

5. The method as claimed in claim 4, wherein the reference scale comprises a series of colour patches of increasing intensity wherein each patch corresponds to an ascending level of harshness of the surfactant.

6. The method as claimed in claim 1, which comprises the additional step of making a product recommendation based on the harshness of the surfactant.

7. The method as claimed in claim 1, wherein the surfactant is a mixture of two or more surfactants.

8. The method as claimed in claim 1, wherein the surfactant is comprised in a hair treatment composition.

9. The method as claimed in claim 8, wherein the hair treatment composition is a shampoo.

10. The method as claimed in claim 1, which further comprises a step of capturing one or more images of one or more steps of the method and storing and/or transmitting the one or more images.

11. The method as claimed in claim 1, wherein the first colour measurement and the second colour measurement of the aqueous solution is performed using CIEL*a*b* on a spectrometer.

\* \* \* \* \*